(12) United States Patent
Becker et al.

(10) Patent No.: US 10,843,992 B2
(45) Date of Patent: Nov. 24, 2020

(54) HYDROFORMYLATION REACTION PROCESS

(71) Applicant: Dow Technology Investments LLC, Midland, MI (US)

(72) Inventors: Michael C. Becker, Hewitt, TX (US); Donald L. Campbell, Carmel, IN (US); Irvin B. Cox, The Villages, FL (US); Shankhadeep Das, Houston, TX (US); Seshadri Kumar, Pune (IN); Glenn A. Miller, South Charleston, WV (US); Nilesh Parmar, Mumbai (IN); George R. Phillips, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 16/611,357

(22) PCT Filed: Jun. 19, 2018

(86) PCT No.: PCT/US2018/038216
§ 371 (c)(1),
(2) Date: Nov. 6, 2019

(87) PCT Pub. No.: WO2018/236823
PCT Pub. Date: Dec. 27, 2018

(65) Prior Publication Data
US 2020/0140361 A1    May 7, 2020

(30) Foreign Application Priority Data
Jun. 23, 2017   (IN) .............................. 201741022124

(51) Int. Cl.
| | | |
|---|---|---|
| *C07C 45/50* | (2006.01) | |
| *B01J 19/00* | (2006.01) | |
| *B01J 19/18* | (2006.01) | |
| *B01J 4/00* | (2006.01) | |
| *B01F 3/04* | (2006.01) | |

(52) U.S. Cl.
CPC .......... *C07C 45/50* (2013.01); *B01F 3/04099* (2013.01); *B01J 4/004* (2013.01); *B01J 19/0066* (2013.01); *B01J 19/1806* (2013.01); *B01J 2219/00779* (2013.01); *B01J 2219/185* (2013.01); *B01J 2219/1943* (2013.01); *B01J 2219/332* (2013.01)

(58) Field of Classification Search
CPC ....... C07C 45/50; B01J 4/004; B01J 19/1806; B01J 19/0066; B01F 3/04099
See application file for complete search history.

(56) References Cited

U.S. PATENT DOCUMENTS

| | | | |
|---|---|---|---|
| 2,804,478 A | * | 8/1957 | Negromanti ............ C07C 45/50 568/451 |
| 4,523,036 A | | 6/1985 | Cornils et al. |
| 4,683,122 A | | 7/1987 | Concordia et al. |
| 5,312,996 A | | 5/1994 | Packett |
| 5,367,106 A | | 11/1994 | Unruh et al. |
| 5,731,472 A | | 3/1998 | Leung et al. |
| 5,741,944 A | | 4/1998 | Bryant et al. |
| 5,763,678 A | | 6/1998 | Beckers et al. |
| 5,929,289 A | | 7/1999 | Abatjoglou et al. |
| 5,932,772 A | | 8/1999 | Argyropoulos et al. |
| 5,952,530 A | | 9/1999 | Argyropoulos et al. |
| 6,090,987 A | | 7/2000 | Billig et al. |
| 6,642,420 B1 | | 11/2003 | Zehner et al. |
| 7,446,231 B2 | | 11/2008 | Peterson et al. |
| 7,939,694 B2 | | 5/2011 | Hong et al. |
| 8,389,774 B2 | | 3/2013 | Becker et al. |
| 8,404,903 B2 | | 3/2013 | Cox et al. |
| 8,673,244 B2 | | 3/2014 | Ko et al. |
| 2014/0350305 A1 | | 11/2014 | Becker et al. |

FOREIGN PATENT DOCUMENTS

| | | |
|---|---|---|
| CN | 102030622 A | 4/2011 |
| CN | 102826970 A | 12/2012 |
| EP | 2152655 A1 | 2/2010 |
| KR | 2013036030 | 4/2013 |
| KR | 1342741 | 12/2013 |

(Continued)

OTHER PUBLICATIONS

Grenville et al. "Blending of Miscible Liquids" (Jan. 1, 2004), XP055506474, p. 507-542 (provided by Applicants on Jan. 9, 2020).*
Grenville, Blending of Miscible Liquids, 2004, p. 507-542.
PCT/US2018/038216, International Search Report and Written Opinion dated Sep. 20, 2018.
PCT/US2018/038216, International Preliminary Report on Patentability dated Jan. 2, 2020.

*Primary Examiner* — Yong L Chu

(57) ABSTRACT

In one aspect, a hydroformylation reaction process comprises contacting an olefin, hydrogen, and CO in the presence of a homogeneous catalyst in a cylindrical reactor to provide a reaction fluid, wherein the reactor has a fixed height, and wherein a total mixing energy of at least 0.5 kW/m3 is delivered to the fluid in the reactor; removing a portion of the reaction fluid from the reactor; and returning at least a portion of the removed reaction fluid to the reactor, wherein the returning reaction fluid is introduced in at least two return locations positioned at a height that is less than 80% of the fixed height, wherein the at least two return locations are positioned above a location in the reactor where hydrogen and carbon monoxide are introduced to the reactor, and wherein at least 15% of the mixing energy is provided by the returning reaction fluid.

15 Claims, 7 Drawing Sheets

(56) References Cited

FOREIGN PATENT DOCUMENTS

| WO | 2012/008717 A2 | 1/2012 |
| WO | 2013/095766 A1 | 6/2013 |
| WO | 2015/047723 A1 | 4/2015 |

* cited by examiner

HYDROFORMYLATION REACTION PROCESS

FIELD

The present invention relates generally to hydroformylation reaction processes.

INTRODUCTION

Hydroformylation is the reaction of olefins with $H_2$ and CO in the presence of an organophosphorous ligand-modified homogeneous rhodium catalyst to produce aldehydes according to the following equation:

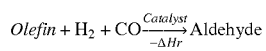

$$Olefin + H_2 + CO \xrightarrow[-\Delta Hr]{Catalyst} Aldehyde$$

Typically the hydroformylation reaction is carried out in the liquid phase where syngas (a gaseous mixture of $H_2$ and CO) is sparged into the reaction fluid containing the liquid olefin, product aldehyde, heavies, and the homogeneous rhodium/ligand catalyst.

In order for the reaction to occur, $H_2$ and CO must be dissolved in the reaction fluid—hence effective gas/liquid mixing is critical to both initiate and maintain the hydroformylation reaction.

In addition, the heat generated by the exothermic hydroformylation reaction must be removed and the reactor temperature controlled at desired reaction conditions. This is typically achieved by internal cooling coils or recirculating the reaction fluid through an external heat exchanger and returning the cooled reaction fluid to the reactor.

Furthermore, under the same conditions as the above hydroformylation reaction, the resulting aldehyde may react further and be hydrogenated in situ to give the corresponding alcohol, and the hydroformylation under aminating conditions can be considered a variant of a hydroformylation reaction.

Another secondary catalytic activity of some hydroformylation catalysts is the hydrogenation or isomerization of double bonds, for example of olefins having internal double bonds, to saturated hydrocarbons or α-olefins, and vice versa. It is important to avoid these secondary reactions of the hydroformylation catalysts to establish and maintain specific hydroformylation reaction conditions in the reactor. Even small deviations from the process parameters can lead to the formation of considerable amounts of undesired secondary products, and maintaining virtually identical process parameters over the volume of the entire reaction liquid volume in the hydroformylation reactor may therefore be of considerable importance.

In general, in the hydroformylation of olefins with organophosphorous ligand-modified homogeneous rhodium catalysts, it is advantageous to establish an optimum concentration of hydrogen and carbon monoxide dissolved in the liquid reaction medium.

The concentration of dissolved carbon monoxide (CO) in the reaction liquid is especially important and is a key hydroformylation reactor control variable. While the dissolved CO concentration in the reaction liquid cannot be measured directly, it is typically monitored and approximated using an on-line analyzer to measure the CO partial pressure in the vapor space of the reactor which is presumed to be in equilibrium with the reaction liquid phase. This approximation improves if the reaction fluid in the reactor is more uniformly mixed and better approximates the CSTR model.

The hydrocarbon (paraffin) formation reaction, the formation of high-boiling condensates of the aldehydes (i.e. high boilers), as well as the degradation rate of the organophosphorous-Rh based catalyst are also influenced by the reaction temperature. It is important to avoid the formation of gradients with respect to the reaction temperature and the concentration of dissolved CO within the volume of the reaction liquid present in the reactor; in other words, it is important for close to identical operating conditions to be established and maintained over the total liquid volume. Thus, it is necessary to avoid non-homogenous distribution of reagents and temperature within a reaction zone.

It is therefore desirable to have a hydroformylation reactor design that provides highly dispersed and uniform syngas and temperature distribution in the reactor and maintains control of the reactor temperature while providing acceptable energy usage.

SUMMARY

The present invention generally relates to processes for the preparation of aldehydes and/or alcohols by reacting olefins in the liquid phase with carbon monoxide and hydrogen gases, a part of these gases being dispersed in the form of gas bubbles in a reaction liquid and another part being dissolved in the reaction liquid, in the presence of a catalyst at elevated temperatures of 50° C. to 145° C. and at pressures of 1 to 100 bar. Embodiments of the present invention advantageously provide thorough gas-liquid mixing of a reaction fluid in a reactor without the use of a mechanical agitator, or in some embodiments, in addition to a mechanical agitator.

It has been found that high velocity fluid flow can be utilized to form internal flows at the middle to bottom of the reactor in the form of directed liquid jets, in some embodiments, to impart momentum and shear into the reaction liquid to not only mix the reactor contents but also to disperse the syngas bubbles produced by a conventional gas sparger. Despite not being at the top of the reactor as in prior venturi gas/liquid mixing reactor designs, with some embodiments of the inventive design, the overall reactor fluid can achieve remarkably uniform temperature and gas-liquid mixing as evidenced by higher and more uniform gas fraction or gas loading and constant temperature in the reactor.

In one embodiment, a hydroformylation reaction process comprises contacting an olefin, hydrogen, and carbon monoxide in the presence of a homogeneous catalyst in a cylindrical reactor to provide a reaction fluid, wherein the cylindrical reactor has a fixed height, and wherein a total mixing energy of at least 0.5 kW/m³ is delivered to the fluid in the cylindrical reactor; removing a portion of the reaction fluid from the cylindrical reactor; and returning at least a portion of the removed reaction fluid to the cylindrical reactor, wherein the returning reaction fluid is introduced in at least two return locations positioned at a height that is less than 80% of the fixed height wherein the at least two return locations are positioned above a location in the reactor where hydrogen and carbon monoxide are introduced to the reactor, wherein at least 15% of the mixing energy is provided by the returning reaction fluid.

These and other embodiments are described in more detail in the Detailed Description.

DETAILED DESCRIPTION

Figure 1:
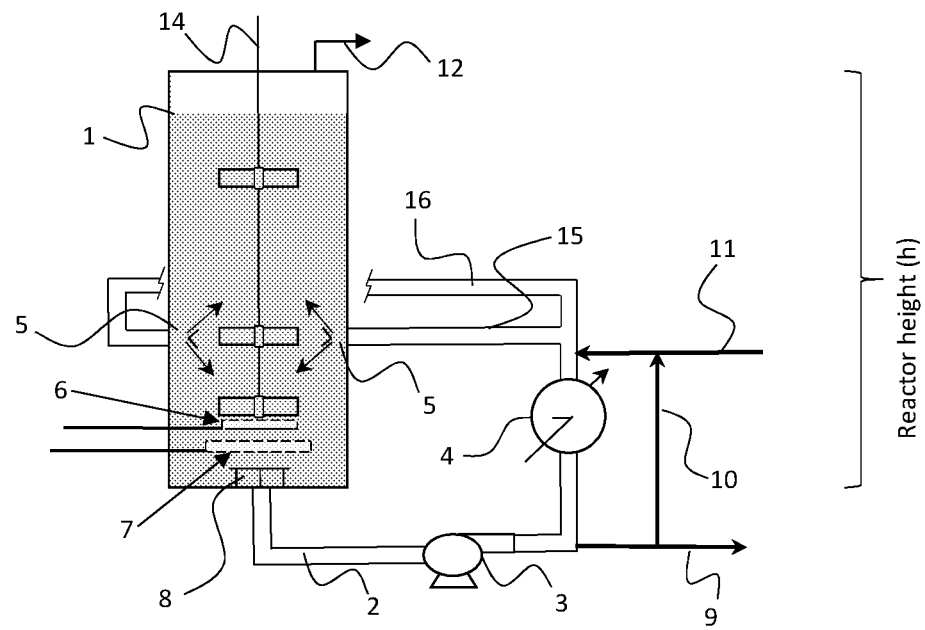
FIG. 1 is a flow sheet illustrating a system for performing a hydroformylation reaction process according to one embodiment of the present invention.

A hydroformylation process generally comprises contacting CO, $H_2$, and at least one olefin under hydroformylation conditions sufficient to form at least one aldehyde product in the presence of a catalyst comprising, as components, a transition metal and an organophosphorous ligand. Optional process components include an amine and/or water.

All references to the Periodic Table of the Elements and the various groups therein are to the version published in the CRC Handbook of Chemistry and Physics, 72nd Ed. (1991-1992) CRC Press, at page 1-10.

Unless stated to the contrary or implicit from the context, all parts and percentages are based on weight and all test methods are current as of the filing date of this application. As used herein, the term "ppmw" means parts per million by weight. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants (e.g., hydrogen, carbon monoxide, olefin), (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). It should be understand that the reaction fluid can be a mixture of gas and liquid. For example, the reaction fluid can include gas bubbles (e.g., hydrogen and/or CO and/or inerts) entrained within a liquid or gases (e.g. hydrogen and/or CO and/or inerts) dissolved in the liquid. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid on its way to an external cooler, (i) a fluid in an external cooler, (j) a fluid being returned to a reaction zone from an external cooler, and (k) ligand decomposition products and their salts.

A solvent advantageously is employed in embodiments of the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g. nitrobenzene), ethers (e.g. tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described, for example, in U.S. Pat. Nos. 4,148,830 and 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Hydrogen and carbon monoxide may be obtained from any suitable source, including petroleum cracking and refinery operations. Syngas mixtures are a preferred source of hydrogen and CO. Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and usually between 1:10 and 10:1. Syngas is commercially available and is often used as a fuel source or as an intermediate for the production of other chemicals. The $H_2$:CO molar ratio for chemical production is often between 3:1 and 1:3 and usually is targeted to be between about 1:2 and 2:1 for most hydroformylation applications.

Embodiments of the present invention are applicable to improving any conventional continuous mixed gas/liquid phase CSTR rhodium-phosphorus complex catalyzed hydroformylation process for producing aldehydes, which process is conducted in the presence of free organophosphorus ligand. Such hydroformylation processes (also called "oxo" processes) and the conditions thereof are well known in the art as illustrated, e.g., by the continuous liquid recycle process of U.S. Pat. No. 4,148,830, and phosphite-based processes of U.S. Pat. Nos. 4,599,206 and 4,668,651. Also included are processes such as described in U.S. Pat. Nos. 5,932,772 and 5,952,530. Such hydroformylation processes in general involve the production of aldehydes by reacting an olefinic compound with hydrogen and carbon monoxide gas in a liquid reaction medium which contains a soluble rhodium-organophosphorus complex catalyst, free organophosphorus ligand and higher boiling aldehyde condensation by-products. In general, rhodium metal concentrations in the range of from about 10 ppm to about 1000 ppm by weight, calculated as free metal, should be sufficient for most hydroformylation processes. In some processes, about 10 to 700 ppm by weight of rhodium is employed, often, from 25 to 500 ppm by weight of rhodium, calculated as free metal.

Accordingly, as in the case of the rhodium-organophosphorus complex catalyst, any conventional organophosphorus ligand can be employed as the free ligand and such ligands, as well as methods for their preparation, are well known in the art. A wide variety of organophosphorous ligands can be employed with the present invention. Examples include, but are not limited to, phosphines, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P(III) moieties such as polyphosphites, polyphosphoramidites, etc. and mixed P(III) moieties such as phosphite-phosphoramidites, fluorophosphite-phosphites, and the like. Of course, mixtures of such ligands can also be employed, if desired. Thus, the hydroformylation process of this invention may be carried out in any excess amount of free phosphorus ligand, e.g., at least 0.01 mole of free phosphorus ligand per mole of rhodium metal present in the reaction medium. The amount of free organophosphorus ligand employed, in general, merely depends upon the aldehyde product desired, and the olefin and complex catalyst employed. Accordingly, amounts of free phosphorus ligand present in the reaction medium ranging from about 0.01 to about 300 or more per mole of rhodium (measured as the free metal) present should be suitable for most purposes. For example, in general, large amounts of free triarylphosphine ligand, e.g., triphenylphosphine, such as more than 50 moles or, in some cases, more than 100 moles of free ligand per mole of rhodium have been employed to achieve satisfactory catalytic activity and/or catalyst stabilization, while other phosphorus ligands, e.g., alkylarylphosphines and cycloalkylarylphosphines may help provide acceptable catalyst stability and reactivity without unduly retarding the conversion rates of certain olefins to aldehydes when the amount of free ligand present in the reaction medium is as little as 1 to 100 and, in some cases, 15 to 60 moles per mole of rhodium present. In addition, other phosphorus ligands, e.g., phosphines, sulfonated phosphines, phosphites, diorganophosphites, bisphosphites, phosphoramidites, phosphonites, fluorophosphites, may help provide acceptable catalyst stability and reactivity without unduly retarding the conversion rates of certain olefins to aldehydes when the amount of free ligand present in the reaction medium is as little as 0.01 to 100 and, in some cases, 0.01 to 4 moles per mole of rhodium present.

More particularly, illustrative rhodium-phosphorus complex catalysts and illustrative free phosphorus ligands include, e.g., those disclosed in U.S. Pat. Nos. 3,527,809; 4,148,830; 4,247,486; 4,283,562; 4,400,548; 4,482,749; European Patent Applications, Publication Nos. 96,986; 96,987 and 96,988 (all published Dec. 28, 1983); PCT patent application, Publication No. WO 80/01690 (published Aug. 21, 1980) and U.S. application Ser. No. 581,352, filed Feb. 17, 1984 and Ser. No. 685,025, filed Dec. 28, 1984. Among the more preferred ligands and complex catalysts that may be mentioned are, e.g., the triphenylphosphine ligand and rhodium-triphenylphosphine complex catalysts of U.S. Pat. Nos. 3,527,809 and 4,148,830 and 4,247,486; the alkylphenylphosphine and cycloalkylphenylphosphine ligands, and rhodium-alkylphenylphosphine and rhodium-cycloalkylphenylphosphine complex catalysts of U.S. Pat. No. 4,283,562; and the diorganophosphite ligands and rhodium-diorganophosphite complex catalysts of U.S. Pat. Nos. 4,599,206 and 4,668,651.

As further noted above, the hydroformylation reaction is typically carried out in the presence of higher boiling aldehyde condensation by-products. It is the nature of such continuous hydroformylation reactions employable herein to produce such higher boiling aldehyde by-products (e.g., dimers, trimers and tetramers) in situ during the hydroformylation process as explained more fully, e.g., in U.S. Pat. Nos. 4,148,830 and 4,247,486. Such aldehyde by-products provide an excellent carrier for the liquid catalyst recycle process. For example, initially the hydroformylation reaction can be effected in the absence or in the presence of small amounts of higher boiling aldehyde condensation by-products as a solvent for the rhodium complex catalyst, or the reaction can be conducted in the presence of upwards of 70 weight percent, or even as much as 90 weight percent, and more of such condensation by-products, based on the total liquid reaction medium. In general, ratios of aldehyde to higher boiling aldehyde condensation by-products within the range of from about 0.5:1 to about 20:1 by weight should be sufficient for most purposes. Likewise it is to be understood that minor amounts of other conventional organic co-solvents may be present if desired.

While the hydroformylation reaction conditions may vary over wide limits, as discussed above, in general it is more preferred that the process be operated at a total gas pressure of hydrogen, carbon monoxide and olefinic unsaturated starting compound of less than about 3100 kiloPascals (kPa) and more preferably less than about 2415 kPa. The minimum total pressure of the reactants is not particularly critical and is limited mainly only by the amount of reactants necessary to obtain a desired rate of reaction. More specifically, the carbon monoxide partial pressure of the hydroformylation reaction process of this invention can be from about 1 to 830 kPa and, in some cases, from about 20 to 620 kPa, while the hydrogen partial pressure can be from about 30 to 1100 kPa and, in some cases, from about 65 to 700 kPa. In general, the $H_2$:CO molar ratio of gaseous hydrogen to carbon monoxide may range from about 1:10 to 100:1 or higher, about 1:1.4 to about 50:1 in some cases.

Further, as noted above, the hydroformylation reaction process of this invention may be conducted at a reaction temperature from about 50° C. to about 145° C. However, in general, hydroformylation reactions at reaction temperatures of about 60° C. to about 120° C., or about 65° C. to about 115° C., are typical.

Of course it is to be understood that the particular manner in which the hydroformylation reaction is carried out and particular hydroformylation reaction conditions employed are not narrowly critical to the subject invention and may be varied widely and tailored to meet individual needs and produce the particular aldehyde product desired.

External cooling loops (pumped circulation of the reactor contents through an external heat exchanger (cooler)) are typically used for highly exothermic hydroformylation reactions such as for lower carbon olefins (C2 to C5) since internal cooling coils alone often lack sufficient heat removal capacity (limited heat transfer area per coil volume). In addition, internal cooling coils displace internal reactor volume making the reactor size larger for a given production rate. However, in some embodiments, at least one internal cooling coil is positioned inside the reactor. Such internal cooling coil(s) can be in addition to an external cooling loop, in some embodiments.

Preferred examples of the olefins used in the present invention include ethylene, propylene, butene, 1-hexene, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene, 2-pentene, 2-hexene, 2-heptene, 2-ethyl hexene, 2-octene, styrene, 3-phenyl-1-propene, 1,4-hexadiene, 1,7-octadiene, 3-cyclohexyl-1-butene, allyl acetate, allyl butyrate, methyl methacrylate, vinyl methyl ether, vinyl ethyl ether, allyl ethyl ether, n-propyl-7-octenoate, 3-butenenitrile, 5-hexenamide, 4-methyl styrene, 4-isopropyl styrene, and the like. Mixtures of isomers (e.g., butene raffinates) can also be employed. The resulting aldehydes products may be subjected to hydrogenation, and thus converted into corresponding alcohols which may be used as a solvent or for the preparation of plasticizer, or may undergo other subsequent reactions such as aldol condensation to higher aldehydes, oxidation to the corresponding acids, or esterification to produce the corresponding acetic, propionic, or acrylic esters.

The olefin starting material is introduced to the reactor by any convenient technique either as a gas (optionally with the incoming syngas feed), as a liquid in the reactor, or as part of a recirculation loop prior to entry into the reactor. One particularly useful method is to use a separate olefin sparger next to or below the syngas sparger (discussed below) to introduce the olefin and syngas feeds in close proximity to each other.

To provide context for the location where hydrogen and carbon monoxide (e.g., as syngas) can be introduced, reference will now be made to the reactor 1 shown in FIG. 1 (FIG. 1 is discussed in more detail below). The reactor 1 shown in FIG. 1 is a cylindrical reaction vessel that includes reaction fluid. The reactor 1 has a fixed height (h) which is the distance between the bottom of the reactor and the top of the reactor. The location of certain features in embodiments of processes of the present invention may be given relative to the fixed height of a reaction vessel. As used herein, the term "fixed height" refers to the distance between the bottom of the reaction vessel and the top of the reaction vessel and can be readily ascertained for a particular reactor. A location that is at 20% of the fixed height of the reaction vessel means that the location is 20% of the fixed height when measured from the bottom of the reaction vessel (a location at 0% of the fixed height is at the bottom of the reaction vessel and a location at 100% of the fixed height is at the top of the reaction vessel).

The syngas is introduced to the reaction by a conventional gas sparger that is positioned in the reaction vessel at a height of 20% or less of the fixed height (e.g., in the lower 20% of the reaction vessel). In some embodiments, the syngas sparger is positioned in the reaction vessel at a height of 10% or less of the fixed height such as at a location proximate the bottom of the reaction vessel. The syngas sparger is often a plate, a ring or series of concentric rings, and the designs of such gas spargers are well known in the art. In general, such syngas spargers should be designed to introduce bubbles of a suitable size and to provide the desired syngas flow contemplated for the olefin flow rate. In some embodiments, the syngas sparger for use in hydroformylation reaction processes of the present invention introduces the syngas in a manner to form discrete bubbles of less than 15 mm in diameter. In some embodiments, the syngas sparger for use in hydroformylation reaction processes of the present invention introduces the syngas in a manner to form discrete bubbles of less than 10 mm in diameter. The use of rings, concentric rings, plates, and other designs are not critical to the present invention other than to deliver suitable bubble sizes. Multiple syngas spargers may be employed as well although one may be suitable.

Also important to generating and maintaining suitable bubble size is sufficient turbulence in the reaction fluid to prevent the bubbles from coalescing and to introduce shear to create smaller bubbles. This has been traditionally accomplished by mixing the reaction fluid with conventional agitators but we have discovered that directed flow (jets) of fluid, preferably catalyst-containing reaction fluid, can be equally effective. We have further found that a combination of these two methods is effective as long as the sum of the power delivered per unit volume by the agitator and the recirculation pump(s) exceeds 0.5 kW/m$^3$. In the absence of the above, the lower (or zero) turbulence in the reaction fluid results in larger diameter gas bubbles sizes which quickly rise up to the gas/liquid interface due to increased buoyancy forces and disengage from the liquid, resulting in lower gas holdup in the reactor. Generating and maintaining small bubbles are important to producing a uniform reaction fluid which will give better gas/liquid mixing, gas hold-up and more reproducible reactor performance. Smaller bubbles allow for maximum gas hold-up and maximize mass transfer area between the bubbles and the liquid for dissolving the syngas (optimized gas volume/surface ratio).

The location of the syngas sparger relative to the recirculation loop outlet nozzle, which is located on the bottom or side of the reactor, should be such that minimal amounts of the syngas bubbles are introduced into the external recirculation loop flow through the pump, piping and external cooler (discussed below) as this can negatively impact pump operation (cavitation, vibration, slugging) and may cause variations in heat exchanger performance and therefore reactor temperature control. The use of an outlet baffle or some other device that impedes and diverts direct streamlines away from the recirculation outlet nozzle of the reactor is a preferred option.

Vertical baffles attached to the interior walls of the reactor provide further mixing and minimize rotational flow by shearing and lifting radial streamlines from the vessel wall.

Without being bound by theory, the high liquid velocity and thorough mixing with small (<15 mm) initial bubble size provided by embodiments of the present invention minimize syngas bubble coalescence, promotes bubble size reduction by shearing and give an even distribution of gas/liquid and temperature throughout the reactor. The movement of small syngas bubbles due to their natural buoyancy up to and across the liquid interface in to the reactor vapor space is countered by the viscosity of the liquid and the turbulent flow of the liquid mass. Excessively large bubbles will rise too rapidly thus resulting in low gas holdup and non-uniform distribution. Despite not being located at the top of the reactor body, the nozzles or flow diverters used in some embodiments of the present invention to create liquid jets which provide a downward and countercurrent flow to counterbalance the natural buoyancy of the bubbles and maintain entrainment of the bubbles in the liquid circulating throughout the reactor, which results in a more uniform distribution of the syngas bubbles throughout the liquid phase. As the syngas dissolves and reacts, the bubbles will shrink which further helps in maintaining their distribution within the liquid phase and in promoting good gas mass transfer into the liquid phase.

In one embodiment, the present invention provides a hydroformylation reaction process that comprises contacting an olefin, hydrogen, and carbon monoxide in the presence of a homogeneous catalyst in a vertically-oriented cylindrical reactor to provide a reaction fluid, wherein the cylindrical reactor has a fixed height, and wherein a total mixing energy of at least 0.5 kW/m$^3$ is delivered to the fluid in the cylindrical reactor; removing a portion of the reaction fluid from the cylindrical reactor; and returning at least a portion of the removed reaction fluid to the cylindrical reactor, wherein the returning reaction fluid is introduced in at least two return locations positioned at a height that is less than 80% of the fixed reactor height, wherein the at least two return locations are positioned above a location in the reactor where hydrogen and carbon monoxide are provided introduced to the reactor, and wherein at least 15% of the mixing energy is provided by the returning reaction fluid. In some embodiments, at least two return locations comprise one or more nozzles that protrude into the cylindrical reactor a distance of not less than 10% and not greater than 50% of the radius of the cylindrical reactor to direct the flow of the returning reaction fluid.

In some embodiments, the flow of the returning reaction fluid is directed by a flow diverter positioned at each return location. In some embodiments, at least one flow diverter directs the flow of the returning reaction fluid horizontally. In some embodiments, at least one flow diverter directs the flow of the returning reaction fluid vertically. In some embodiments, at least one flow diverter directs the flow of the returning reaction fluid horizontally and at least one flow diverter directs the flow of the returning reaction fluid vertically.

The flow of the returning reaction fluid, in some embodiments, is directed by the flow diverter to prevent inducing rotational flow of the fluid around the center vertical axis of the cylindrical reactor. In some embodiments, the flow of the returning reaction fluid is divided and directed in a plurality of directions that are not toward a center vertical axis of the cylindrical reactor and not perpendicular to the center vertical axis.

In some embodiments, the combination of the flow area of the flow diverter and the flow rate of the returning reaction fluid results in the formation of a jet of fluid inside the cylindrical reactor which imparts momentum and induces mixing in the bulk fluid in the cylindrical reactor and wherein the returning reaction fluid is divided and directed in a plurality of directions.

In some embodiments, hydrogen and carbon monoxide are introduced in the cylindrical reactor at a height that is less than 20% of the fixed height of the reactor, and the return locations are positioned at a height that is less than 80% of the fixed reactor height.

In some embodiments, hydrogen and carbon monoxide are provided as syngas, and the syngas is introduced in such a manner to form discrete bubbles in the size range of less than 15 mm in diameter in the cylindrical reactor.

A plurality of baffles (horizontal and/or vertical) are positioned inside the cylindrical reactor in some embodiments as discussed further herein.

In some embodiments, an agitator is positioned in the cylindrical reactor. In some embodiments where an agitator is positioned in the cylindrical reactor, the agitator and the returning reaction fluid provide the mixing energy in the cylindrical reactor. In some embodiments where an agitator is positioned in the cylindrical reactor, the agitator is not operating and only the returning reaction fluid provides the mixing energy in the cylindrical reactor.

Various embodiments of the present invention may be understood more readily by reference to the accompanying drawings.

FIG. 1 is a flow sheet illustrating a system for performing a hydroformylation reaction process according to one embodiment of the present invention. FIG. 1 shows a cylindrical reactor or reaction vessel 1 having a top, a bottom, and a fixed height (h). The reactor 1 is shown containing a level of reaction fluid and a gas/liquid interface. As shown in FIG. 1, a stream of reaction fluid 2 is withdrawn from near the bottom of reactor 1 via pump 3. The stream is sent to return nozzles 5 after passing through a heat exchanger 4 and/or bypass line 10. An agitator 14 with both a radial flow disk blade gas dispersion and liquid pumping impeller is shown in the embodiment of FIG. 1, although as set forth herein, an agitator is not required in all embodiments of the present invention. Further, even in embodiments where an agitator is present, the agitator may be operating in some embodiments and not operating in other embodiments. When present, and as shown in FIG. 1, an agitator is typically located at a vertical center line of the reactor 1.

The reaction fluid 2 that is removed from the bottom of the reactor 1 is returned to the reactor via two or more nozzles 5. The two or more nozzles 5, in some embodiments, can be oriented in symmetrical pairs, symmetrical triads or other symmetrical arrangements. The recirculation flow exiting these nozzles and entering the bulk reactor fluid form one or more liquid jets of returning reaction fluid which impart momentum and gas/liquid mixing in the bulk reactor fluid. As discussed further in connection with FIGS. 2-4, the nozzles 5 can be oriented so as to direct the liquid jets in a downward or upward direction. In some embodiments, the nozzles can be oriented such that the liquid jets are not directed toward a center vertical axis of the reactor 1 (e.g., not toward the reactor center line or toward the reactor agitator shaft and impellers 14 in FIG. 1). It is preferred that the liquid jets are not oriented in a strictly horizontal or strictly vertical direction or directly toward the vertical axis or center of the agitator or toward the reactor agitator shaft or impellers (i.e., a and β, discussed below, are both greater than zero). In some embodiments, multiple sets of symmetrical nozzles can be positioned at different nozzle orientations (radial position) and/or different heights in the reactor 1.

Syngas is introduced to the reactor 1 via stream 6 with the syngas sparger. Likewise, the olefin is introduced via stream 7. The olefin can also be introduced via a sparger apparatus in some embodiments. In some embodiments, the olefin can be mixed with syngas or stream 11 prior to introduction in the reactor 1. An outlet baffle 8 is used to minimize entrained gases from entering line 2 in the embodiment shown in FIG. 1, although an outlet baffle is not used in other embodiments.

With regard to the reaction fluid stream 2 removed from the bottom of the reactor, crude product and a catalyst mixture can be removed from stream 2 as represented by stream 9. While in FIG. 1, the crude product/catalyst mixture stream 9 is shown as being separated from the recirculation stream 2, in other embodiments, a stream of reaction fluid can be withdrawn from a different location(s) in the reactor 1 and processed to separate a crude product/catalyst mixture stream. In any event, the stream of crude product and catalyst mixture can be sent to another reactor in some embodiments, or to a catalyst/product separation zone in other embodiments (a catalyst/product separation zone can also follow downstream reactors in embodiments where multiple reactors are used). In the embodiment shown in FIG. 1, recycled catalyst from a catalyst/product separation zone is returned to the reactor 1 via stream 11 by combining the recycled catalyst stream 11 with the flow of reaction fluid being returned to the reactor 1 via the bypass stream 10 and/or the stream leaving the heat exchanger 4. In other embodiments, a portion of the recirculation flow may be removed (Stream 9) for other processing or added to by other process streams (Stream 11) such that Stream 2 does not necessarily have to equal Streams 15 and 16.

As shown in FIG. 1, an optional gas purge stream 12 from the reactor can be vented, flared, or sent to the plant fuel gas header or to another reactor in embodiments where multiple reactors are arranged in series. Analysis of this purge stream 12 can provide a convenient means to measure CO partial pressure in the reactor 1 for reaction control. While not shown in FIG. 1, the system also includes other standard pieces of equipment such as valves, temperature sensors, and pressure sensors, which are easily recognized and implemented by those skilled in the art.

The reaction fluid being returned to the reactor 1 can be introduced in at least two symmetrically opposed return locations (represented by nozzles 5 in FIG. 1). The at least two return locations are positioned at a height that is less than 80% of the fixed height of the reactor but also above the location in the reactor where hydrogen and carbon monoxide are introduced to the reactor (e.g., above the syngas sparger 6 for the embodiment shown in FIG. 1). In some embodiments, at least two return locations are positioned at a height that is less than 60% of the fixed height of the reactor but also above the location in the reactor where hydrogen and carbon monoxide are introduced to the reactor. In some embodiments, at least two return locations are positioned at a height that is less than 50% of the fixed height of the reactor but also above the location in the reactor where hydrogen and carbon monoxide are introduced to the reactor.

The returning reaction fluid can provide at least 15% of the total mixing energy in the reactor. In various embodiments, the returning reaction fluid can provide at least 25% of the total mixing energy, or at least 30% of the total mixing energy, or at least 40% of the total mixing energy, or at least 50% of the total mixing energy, or at least 60% of the total mixing energy, or at least 70% of the total mixing energy, or at least 75% of the total mixing energy, or at least 80% of the total mixing energy, or at least 85% of the total mixing energy, or at least 90% of the total mixing energy, or at least 95% of the total mixing energy. In some embodiments, the returning reaction fluid can provide substantially all or 100% of the total mixing energy to the reactor. It should be understood that the total mixing energy comprises mixing energy provided by an operating agitator (if present), by the liquid jets produced by the returning reaction fluid, or any other source of mixing energy, but does not include any de minimis mixing energy that might be provided by the introduction of the syngas, olefin, or other reactant feed to the reactor. In embodiments where the liquid jets produced by the returning reaction fluid provides substantially all or 100% of the mixing energy, the reactor either does not include an agitator, or includes an agitator that is not in operation. In some embodiments where the liquid jets produced by the returning reaction fluid do not provide 100% of the mixing energy, an operating agitator in the reactor can provide the balance of the mixing energy.

As used herein, the total mixing energy provided to a reactor is measured by calculating the mixing energy imparted by the agitator and the mixing energy imparted by the returning reaction fluid. The mixing energy imparted by the agitator and the returning reaction fluid can be calculated by measuring the voltage and current of the agitator and recirculating pump motors (e.g., agitator 14 and pump 3 in FIG. 1).

Figure 4:
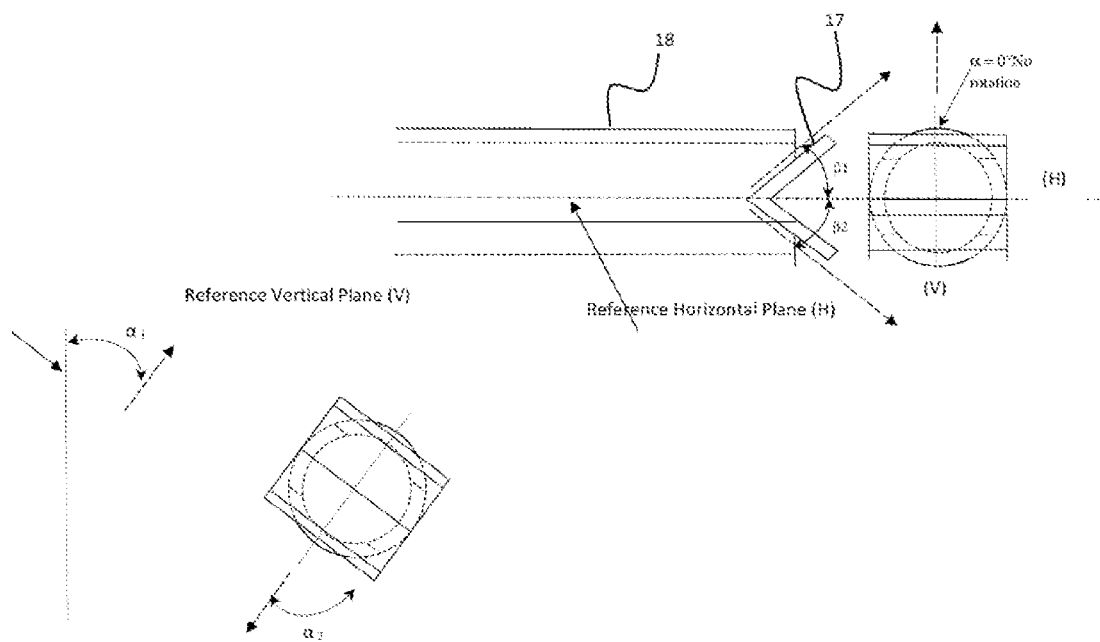
FIG. 4 illustrates the relative placement of one embodiment of a flow diverter that can be used in some embodiments of the present invention.

The manner in which the reaction fluid is returned impacts the effectiveness of the mixing energy provided. In some embodiments, the reaction fluid can be returned using pipes with one or more flow diverter plate(s) 17 are installed on the end of a section of pipe 18 that is then inserted through and attached to the recirculation return nozzle(s) of the reactor as shown in FIG. 4 and discussed further below. In some embodiments, the reaction fluid is returned using nozzles or flow orifices positioned at the end of a section of pipe that is then inserted through and attached to the recirculation return nozzle(s) of the reactor as discussed further below. In each instance, the resulting liquid jet(s) velocity is a function of the flow area of the nozzles or orifices, or the flow area created between the flow diverter plate(s) 17 and the inside wall of the pipe 18, and the mass flow rate and density of the returning reaction fluid. The combination of flow area and flow rate results in a jet of reaction fluid inside the reactor that imparts momentum and induces gas/liquid and liquid/liquid mixing of the bulk fluid in the reactor. Further, the returning reaction fluid is divided and directed in a plurality of directions.

The term "flow diverter" is used herein to encompass both nozzles and diverter plates positioned in reactor recirculation return pipes. In either case, the flow diverters direct the flow of the returning reaction fluid. As discussed further below, the flow diverters direct the flow of the returning reaction fluid horizontally in some embodiments. In some embodiments, the flow diverters direct the flow of the returning reaction fluid vertically. The flow diverters direct the flow of the returning reaction fluid both horizontally and vertically in some embodiments.

In some embodiments, the flow diverters direct the flow of the returning reaction fluid so as to prevent inducing rotational flow around the center vertical axis of the reactor (e.g., the axis corresponding to the shaft of the agitator 14 shown in FIG. 1).

In some embodiments, the flow of the returning reaction fluid is divided and directed in a plurality of directions that are not toward a center vertical axis of the reactor and not perpendicular and not parallel to the center vertical axis. This feature can be important in some embodiments where the reactor includes an agitator (either operating or not). For example, directing the recirculation return flow toward the shaft of the agitator could induce vibration and cause damage to the agitator, agitator seal or steady bearing.

Figures 2, 3:
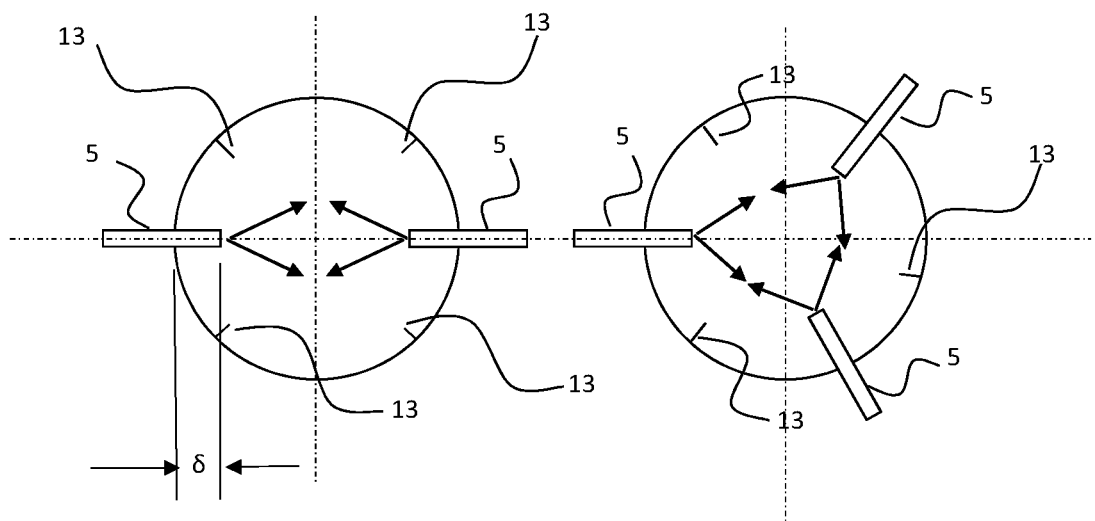
FIG. 2 is a top, cross-sectional view illustrating a cylindrical reactor that can be used in some embodiments of the present invention.
FIG. 3 is a top, cross-sectional view illustrating another cylindrical reactor that can be used in some embodiments of the present invention.

FIG. 2 shows a top sectional view of an arrangement of two flow diverters 5 in a reactor according to one embodiment of the present invention. FIG. 3 shows a top sectional view of an arrangement of three flow diverters 5 according to another embodiment of the present invention. FIGS. 2 and 3 each illustrate how the flow diverters direct the liquid jets formed by the recirculation return flow. Other arrangements of flow diverters can be selected (e.g., four or more flow diverters and/or different location of flow diverters). In some embodiments, the flow diverters are evenly spaced around the circumference of a cylindrical wall of a reactor.

FIGS. 2-4 illustrate the off-set angle of the liquid jets produced by the reactor recirculation fluid as it exits the flow diverters 5. In the embodiments shown, the flow diverters 5 are pipes having flow dividing plates (such as the embodiment shown in the top diagram of FIG. 4) that split the flow leaving each pipe into two liquid jets and with the flow diverter rotated by angle $\alpha$ results in one liquid jet flowing upward and one liquid jet flowing downward.

In embodiments utilizing flow diverters, the orientation of the flow diverters in the pipe and the angles imparted to the returning reaction fluid to provide the liquid jets can be important. FIG. 4 illustrates examples of such orientation and the determination of the direction of flow of the liquid jet(s) of returning reaction fluid.

Turning now to FIG. 4, the vertical directional component of the liquid jet resulting from the flow leaving a flow diverter can be defined relative to a defined horizontal plane (H) by angle, $\beta$ (beta), where:

Angle $\beta 1$ is defined as the angle of the liquid jet exiting the flow diverter above the reference horizontal plane (H) located at the centerline of the reactor nozzle through which the flow diverter is inserted and attached as shown in FIG. 4 and, Angle $\beta 2$ is defined as the angle of the liquid jet exiting the flow diverter below the reference horizontal plane (H) located at the centerline of the reactor nozzle through which the flow diverter is inserted and attached as shown in FIG. 4.

Similarly the horizontal directional component of the liquid jet resulting from the reaction fluid leaving a flow diverter can also be defined relative to a defined vertical plane (V) by angle, $\alpha$ (alpha), where:

Angle $\alpha 1$ is defined as the angle of the liquid jet exiting the flow diverter on one side of the reference vertical plane (V) located at the centerline of the reactor nozzle through which the flow diverter is inserted and attached as shown in FIG. 4.

Angle $\alpha 2$ is defined as the angle of the liquid jet exiting the flow diverter on the opposite side of the reference vertical plane (V) located at the centerline of the reactor nozzle through which the flow diverter is inserted and attached as shown in FIG. 4.

Angle $\alpha$ also represents the degree of rotation of the flow diverter from the vertical plane located at the centerline of the nozzle through which the flow diverter is inserted and attached.

The directions of flow of the liquid jets from the flow diverter relative to a horizontal plane ($\beta$) and a vertical plane ($\alpha$) are key features of some embodiments of the present invention. In some embodiments, the flow diverters can be configured so as to provide returning reaction fluid with $\beta 1$ and $\beta 2$ within the range of 0° to 90° (i.e., offset upward and/or downward relative to the flow diverter) and with $\alpha 1$ and $\alpha 2$ within the range of 0° to 90° (i.e., offset to the left and/or right relative to the flow diverter) with the provision that $\alpha 1$ and $\alpha 2$, as well as $\beta 1$ and $\beta 2$, are not necessarily equal—but can be—and that $\alpha 1$, $\alpha 2$, $\beta 1$, $\beta 2$ are all greater than 0°. In some embodiments, the flow diverters are configured so as to provide an angle $\alpha 1$, $\alpha 2$ from 20° to 60° and an angle $\beta 1$, $\beta 2$ from 20° to 60°. In some embodiments, the flow diverters are configured so as to provide an angle $\alpha 1$, $\alpha 2$ from 25° to 50° and an angle $\beta 1, \beta 2$ from 25° to 50°. It should be understood that the flow of returning fluid will not be in a single line in some embodiments, but that the majority of the stream returning to the reactor in a single flow diverter will be within a relatively narrow range of $\alpha$ and $\beta$ values. For the purposes of this application, when the terms "vertical" and "horizontal" are used in connection with the flow of returning reaction fluid at a fluid diverter, the terms can be understood using angles $\alpha$ and $\beta$, respectively. That is, a "vertical stream" or "vertical jet" is oriented up and/or down at $\beta$ greater than zero but a essentially zero. A "horizontal stream" or "horizontal jet" is oriented going left and/or right at $\beta$ essentially zero but a greater than zero. The term "directed streams" generally refers to streams that have both $\alpha$ and $\beta$ greater than zero.

In some embodiments, additional sets of flow diverters can be provided at the same or different heights as shown in FIG. 1 or at different angles ($\alpha$ and/or $\beta$). As shown in FIG. 3, the outlet of the flow diverter, in some embodiments, can be inserted into the reactor body by a distance ($\delta$) from the reactor wall. In some embodiments, $\delta$ is not greater than 50% of the radius of the cylindrical reactor. In some embodiments, $\delta$ is at least 10% of the radius of the cylindrical reactor. $\delta$ is from 10% to 45% of the radius of the cylindrical reactor in some embodiments. In some embodiments, the end of the flow diverter can be generally flush with the reactor wall such that $\delta$ is ~0% of the radius of the cylindrical reactor.

In some embodiments, the reactor can include vertical baffles. As shown in FIGS. 2 and 3, the vertical baffles 13 can be coupled to the reactor 1 wall. Vertical baffles can advantageously be used in some embodiments to facilitate mixing and/or to prevent an overall circular flow.

Flow diverters for use in embodiments of the present invention can have a number of forms. In some embodiments, a diverter plate is positioned proximate the end of the pipe that returns the reaction fluid to the reactor. FIG. 4 illustrates one embodiment of a diverter plate 17 designed to split the flow of reaction fluid leaving a return pipe 18 vertically (up and down) or horizontally (left and right) if rotated 90°. The particular design of the diverter plates is not critical to the present invention. As shown in FIG. 4, the plates can be simple pieces of metal forming an angle. Alternatively, a simple "T" or "Y" at the end of the return pipe entering the reactor may be employed, or plates may be mounted inside the reactor to divert the flow. In addition, piping reducers, nozzles, tapered ends or pipe caps with orifices drilled can be attached to the end of the return pipes and can be used to create the directional liquid jets rather than flow dividing plates (or flow diverters) as shown in FIG. 4. For the purposes of this application, the term flow diverter includes "nozzles", "jet nozzles", and "diverter plates", and these terms are generally used interchangeably unless clear from the context that only one of them is being discussed.

The present invention can be employed with an active agitator (agitator 14 is shown in FIG. 1) although the direction of liquid jet flow(s) based on (αc) and especially (β) should not interfere with or impact directly upon the agitator blades or shaft as this may generate unacceptable torque or vibration on the agitator. In some embodiments, an agitator 14 may be positioned in the reactor 1, but can be idle (i.e., not operating). In some embodiments, an agitator is not present.

For embodiments where diverter plates are positioned in a return pipe, it should be recognized that the placement of plates within the return line will increase the velocity of the fluid by reducing the cross-sectional flow area of the pipe. The restriction and increase in velocity generates a liquid jet which is generally described as a stream of fluid that is injected into a surrounding medium (bulk reactor fluid) that can travel long distances without dissipating. The shape, direction and length of the liquid jet is a function of many factors such as velocity at the flow diverter, bulk and jet stream fluid viscosity, fluid mass and momentum, shape and direction of the flow diverter, and the unobstructed jet path length. The fluid momentum of the liquid jet flow imparts mixing energy to the bulk reactor fluid by shear forces. It should be understood that the various configurations of the flow diverters (e.g., diverter plates, nozzles, etc.) create a liquid jet or liquid jets in the bulk reactor fluid from the returning reactor fluid. In general, it should be understood that in such embodiments, the combination of the flow area of the flow diverter and the flow rate of the returning reaction fluid results in the formation of a jet of fluid inside the cylindrical reactor which imparts momentum and induces gas/liquid and liquid/liquid mixing in the bulk fluid in the cylindrical reactor.

In embodiments where the flow diverters provide jet flow to the returning reaction fluid, the flow diverters can be oriented to maximize or provide substantial jet path length within the reactor to provide mixing energy. By providing substantial jet path length (i.e., increasing the penetration of the returning reaction fluid within the bulk fluid in the reactor), the returning reaction fluid contacts more of the bulk fluid in the reactor in order to impart additional momentum and thus mixing energy to the bulk fluid. The orientation of the flow diverters can maximize the jet path length, for example, by directing the returning reaction fluid so as to avoid contacting a reactor wall prior to natural dissipation of the jet.

It is the increased velocity resulting from the flow diverter(s) that generates the needed mixing in the reactor and allows for easy retrofit of an existing reactor without substantial capital expense such as in a debottlenecking upgrade.

Surprisingly, it has been found that employing flow diverters as described herein enables the operation of the reactor without an agitator being operated while providing the same level of gas/liquid and liquid/liquid mixing the bulk reactor fluid. Providing an increase in flow of returning reaction fluid can enable stable operation without an operating agitator. To facilitate the increased recirculation flow and additional pressure drop through the flow diverter, a larger pump or larger pump impeller or larger pump motor or multiple pumps may be required as compared to systems where the reaction fluid is only cooled and returned to the reactor using conventional techniques (single recirculation pump). By providing adequate mixing in the reactor without use of an agitator, embodiments of the present invention can advantageously permit continued operation of the reactor if there are issues with an agitator motor, agitator seals, agitator shaft/impeller, steady bearing or similar agitator-related issues until such time as the unit can be shut down and repairs can be made thus avoiding unplanned loss of production.

In order to effect good mixing in the reactor, the amount of energy spent in agitating the bulk fluid in the reactor will not change significantly from a conventional agitator-based design but the mixing energy is introduced in a new manner Since the amount of mixing is well known from prior designs, it is straight forward to calculate the energy required from the pump to generate sufficient flow in embodiments of the present invention. In some embodiments, a total mixing energy of at least 0.5 kW per $m^3$ is delivered to the reaction fluid in the reactor. A total mixing energy of at least 0.7 kW per $m^3$ is delivered to the reaction fluid in the reactor in some embodiments. In some embodiments, a total mixing energy of at least 0.9 kW per $m^3$ is delivered to the reaction fluid in the reactor. As set forth above, the returning reaction fluid, according to some embodiments, can provide at least 15% (and up to 100% in some embodiments) of the total mixing energy in the reactor. In embodiments where the agitator is operating and is then turned off or has its rotational speed reduced, the mixing energy supplied by the returning reaction fluid can be increased by increasing the power provided to the pump, employing a spare pump, activating a larger pump, or similar techniques.

A recirculation flow that is sufficient to remove the heat of reaction via an external heat exchanger will have a substantial flow rate in order for the heat exchanger to operate properly. Excessive flow in general is not detrimental to the heat exchanger operation but may be needed to effect sufficient mixing in the reactor. An optional by-pass line (10) around the heat exchanger can be used to address the heat exchanger limitations. Designing the recirculation flow to impart sufficient momentum to mix the reactor contents will not encompass a significant change from conventional design other than employing very simple flow diverters at the end of the recirculation line as described above.

For new reactors, some embodiments of the present invention can advantageously eliminate the cost of an agitator as well as the need for agitator seals and steady bearings which require maintenance/replacement, and can eliminate seal leaks.

As shown in FIGS. 2 and 3, in some embodiments of the present invention, vertical baffles can be provided in the reactor. In other embodiments, horizontal baffles can be provided in the reactor to generate multiple reaction zones within the main body. Such horizontal baffles are described, for example, in U.S. Pat. No. 5,728,893. In such embodiments, separate return lines and flow diverters for returning reaction fluid can be used in each reaction zone. In some embodiments, the reactor can include both horizontal and vertical baffles while in other embodiments, only horizontal baffles or only vertical baffles are provided.

Some embodiments of the present invention will now be described in detail in the following Examples.

EXAMPLES

Example 1 and Comparative Example A

Figure 5:
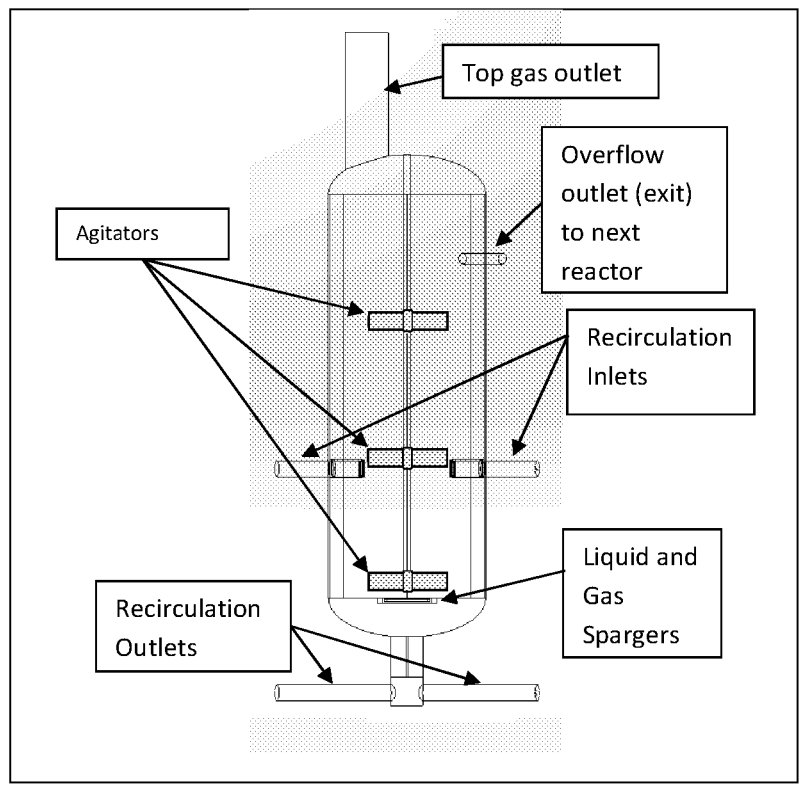
FIG. 5 is a schematic of a reactor design simulated in the Examples according to some embodiments of the present invention.
Figure 6:
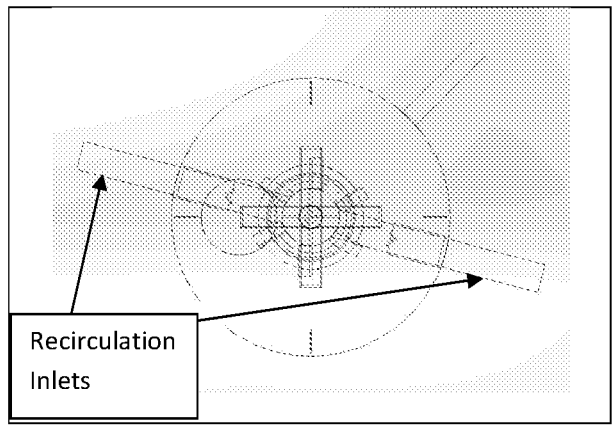
FIG. 6 is a top schematic view of illustrating a system for performing a hydroformylation reaction process according to one embodiment of the present invention.

A Computational Fluid Dynamics (CFD) modeling study was undertaken to establish the mixing efficiency of a conventional CSTR hydroformylation reactor. A schematic of the reaction system is shown in FIGS. 5-6. FIGS. 5-6 show a schematic of the reactor and the location of certain devices. Dimensions and locations of various components are provided in Table 1. The operating pressure is around 16 barg. The density of the liquid propylene is approximately 737 kg/m$^3$ (around 46 lb/ft$^3$), and the density of syngas is approximately 21.5 kg/m$^3$ (1.35 lb/ft$^3$), at this pressure. The feed flow rates of syngas and liquid propylene for all the examples are also given in Table 1. The viscosity of liquid propylene is taken to be 0.0003 Pa·s, and the viscosity of syngas is taken to be 1.8 e$^{-5}$ Pa·s. The gas-liquid surface tension between the syngas and the liquid propylene is taken to be 18 dynes/cm (0.018 N/m), in keeping with typical values for similar organics. The syngas is introduced with a ring sparger located proximate the bottom tangent line of the reactor. The sparger has a diameter of 102 cm with 69 holes having diameters of 7.9 mm each and spaced at 15 mm intervals. The CFD reactor model has a single standard 52 inch diameter gas-distribution turbine located near the bottom of the reactor and two 60 inch diameter pitched-blade liquid mixing agitators located near the middle and top of the reactor operating at ~85 rpm.

The goal of the CFD modeling is to evaluate the gas loading or hold-up of the gas in the liquid as well as uniformity of distribution of the gas where the gas loading or gas hold-up is defined as the % of gas by volume in the reaction fluid and where the sum of the % by volume of gas and the % volume of liquid in the reactor is equal to the total reaction fluid volume. Since only the syngas that is dispersed and dissolved in the reaction fluid can react, it is critical that the syngas introduced to the reactor is quickly dispersed and dissolved into the reaction fluid rather than rising as bubbles to the vapor/liquid interface where it disengages and enters the vapor space of the reactor and is no longer available for reaction. Additionally, volumes within the reactor without dispersed or dissolved syngas are starved for a reactant, and thus do not contribute to the reaction or productivity of the reactor. Many hydrolysable catalysts exhibit catalyst degradation in the absence of syngas at reaction temperatures such that these regions of low dispersed or dissolved syngas will contribute towards decline in catalyst performance. Alternatively, many rhodium phosphine catalysts exhibit degradation in high CO environments such that regions of excessively high dissolved syngas concentrations should also be avoided. Thus, a highly dispersed (high gas hold-up or gas fraction) and uniform gas mixing is the most desirable outcome.

To assess the mixing characteristics of the present invention, it is convenient to examine the gas distributions from the CFD modeling to identify both the uniformity in gas distribution and the extent of gas loading. Commercial experience with well-agitated CSTR reactors have gas loading values in the 5-12% range, preferably above 8%.

CFD modelling programs can be used to predict an overall or average gas loading value for the entire reactor volume but this may de-emphasize localized effects of areas with high or low gas loading and short residence time (e.g., pipe inlets/outlets, near agitator impellers, etc.).

To better assess variation or uniformity in the resulting gas distribution for a particular case being evaluated, it is convenient to not only visually assess the pattern of gas distribution results in the overall reactor volume (i.e. color coded gas fraction or density) but also, to be more quantitative, utilize a small number of horizontal slices of the reactor volume at set uniform intervals from the bottom tangent line (BTL) and calculate the gas fraction in the smaller volumes and compare the standard deviation of the calculated gas distribution values from each section as compared to the overall gas fraction which allow a direct comparison between the CFD modelling results for multiple design cases. Smaller values for the standard deviation are indicative of less variation or a more uniform gas distribution and good gas/liquid mixing. Larger values of standard deviation are indicative of more variation or less uniform gas distribution and less gas/liquid mixing.

Figure 7:
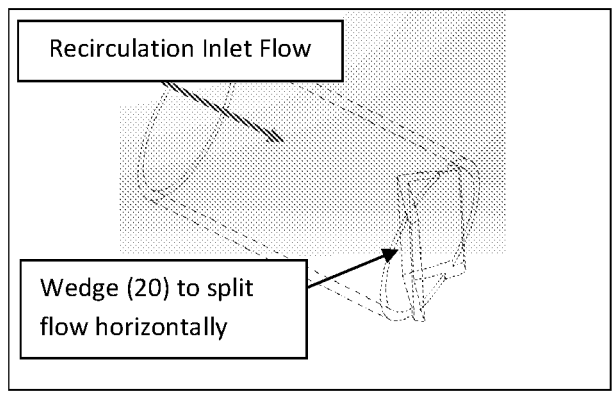
FIG. 7 illustrates one embodiment of a flow diverter that can be used in some embodiments of the present invention.

The results of the CFD modeling of a typical commercial scale hydroformylation reactor with and without a flow diverter are discussed below. In these examples, when a flow diverter is used (Example 1), the flow diverter is a diverter plate positioned on the proximate the end of a return line as illustrated in FIGS. 1, 6, and 7.

TABLE 1

| Dimensions | Base case |
|---|---|
| Reactor diameter (m) | 3 |
| L/D | 3.0 |
| Recirculation diameter (m) | 0.3 |
| Recirculation outlet diameter (m) | 0.3 |
| Straight height of the reactor (m) | 8.9 |
| Recirculation nozzle height above bottom tangent line (m) | 2.4 |
| Length of recirculation nozzle inside reactor(m) (δ) | 0.6 |
| Recirculation flow rate (m^3/s) | 0.32 (1.0x) |
| Syngas Gas feed flow rate (m^3/s) | 0.10 |
| Olefin Liquid feed flow rate (m^3/s) | 0.0048 |

CFD modeling calculations were performed using a reactor system as shown above. The results after 100 seconds (taken as steady state) are compared below. No reaction was assumed and gas/liquid density (as represented by gas fraction) was modeled for simplicity. Horizontal slices taken every meter from the bottom tangent line are used to assess the mixing characteristics of the reactor. Example 1 employed diverter plates with $\alpha 1=90°$ and $\beta 1=\beta 2=45°$ as shown in FIGS. 6 and 7. Comparative Example A did not employ the diverter plates. Comparative Example B was similar to Example 1 except the agitator was not running. In commercial operation with a conventional, multiple agitator impellor design, stable operation (good mixing, reactor temperature control) is observed when the average gas distribution is above 5 vol % gas, preferably above 6 vol % gas, and more preferably above 8 vol % gas. Cases where these conditions were not met exhibited unstable operation (poor mixing, temperature control).

Figure 8:
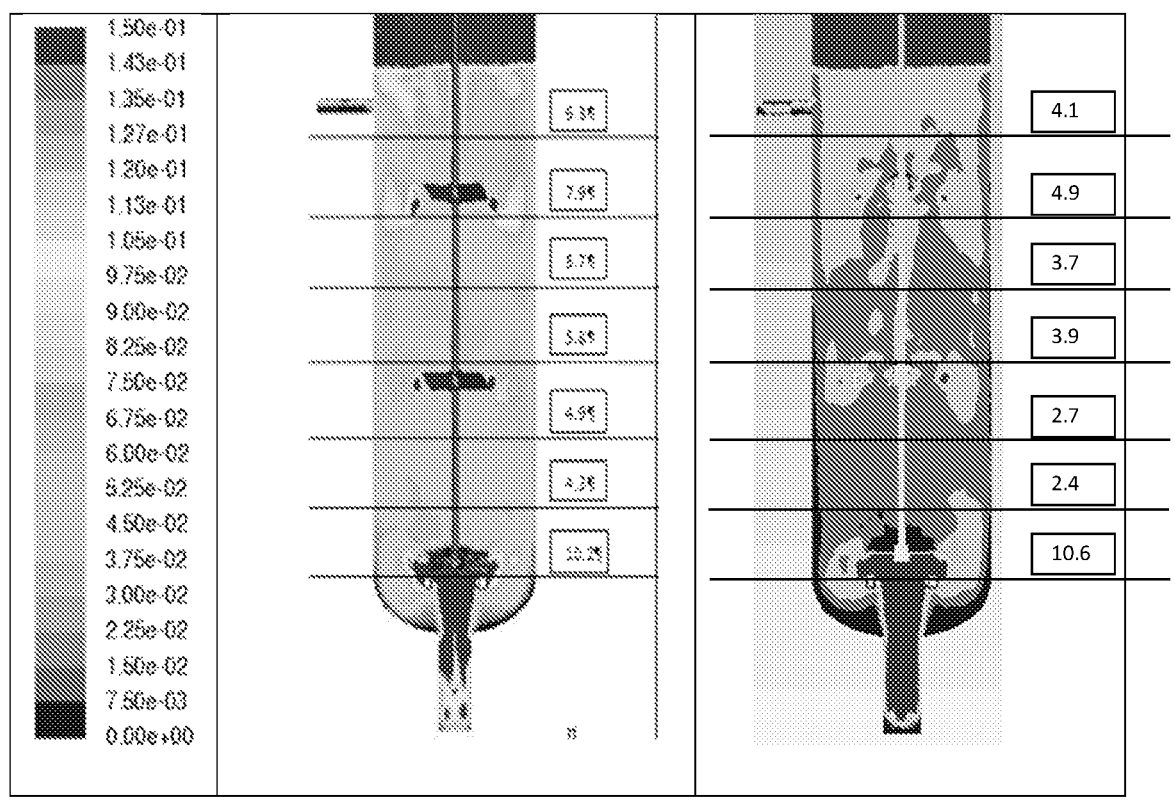
FIG. 8 shows the gas fraction distributions based on the CFD modelling for Example 1 and Comparative Example A.

The results are given Table 2 and shown visually in FIG. 8. In FIG. 8 (as well as FIGS. 9-10), the values shown to the right of the reactor diagrams are percentage of gas fraction for the horizontal slices at 1 meter intervals from the bottom tangent line. The gray scale on the far left is in volume gas fractional units (for example, the medium value is 0.0075 or 7.5%), with uniformly higher numbers on the scale being preferable. In FIG. 8, the gas fraction distribution for Example 1 is shown on the left, and the distribution for Comparative Example A is shown on the right. The overall gas fraction in the reaction fluid in Example 1 is 8.3% compared to Comparative Example A with an overall gas fraction of 5.3%. The average of the horizontal slices is 6.4% in Example 1 (compared to 4.6% in Comparative Example A). The uniformity of the gas/liquid mixing as assessed by the standard deviations of the slices is 2.0 in Example 1 as compared to 2.8 in Comparative Example A. The gas fraction is clearly higher and more evenly distributed in Example 1 (with the flow diverter) as compared to Comparative Example A (no flow diverter).

Examples 2 and 3

Figure 9:
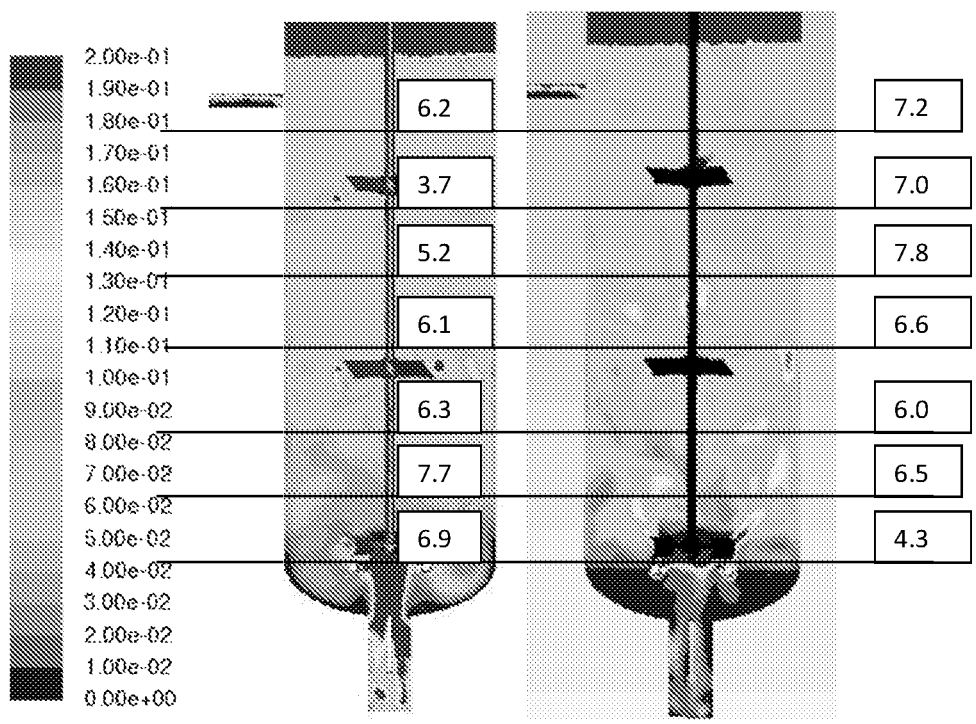
FIG. 9 shows the gas fraction distributions based on the CFD modelling for Examples 2 and 3.

Additional comparative CFD modeling experiments were performed where the recirculation flow of the returning reaction fluid was increased by a factor of 1.73 which models two recirculation pumps in operation. In Example 2 the agitator is running, and the two recirculation pumps (1.73×Example 1 flow=1.73×) are in operation. In Example 3 the agitator is not running, and the two recirculation pumps (1.73×flow) are in operation. The results are shown in FIG. 9 and Table 2. In FIG. 9, the gas fraction distribution for Example 2 (agitator on) is on the left, and the distribution for Example 3 (agitator off) is on the right. In contrast to the results shown above, with the agitator off in Example 3, there was virtually no entrainment into the recirculation loop such that the syngas "hot spot" in the bottom of the reactor is reduced. A remarkably uniform, well mixed reaction fluid is observed despite the lack of an operating, conventional agitator in Example 3. In addition, despite using two pumps, not having the agitator running results in less total energy needed in Example 3 compared to the other Examples.

Example 4

Figure 10:
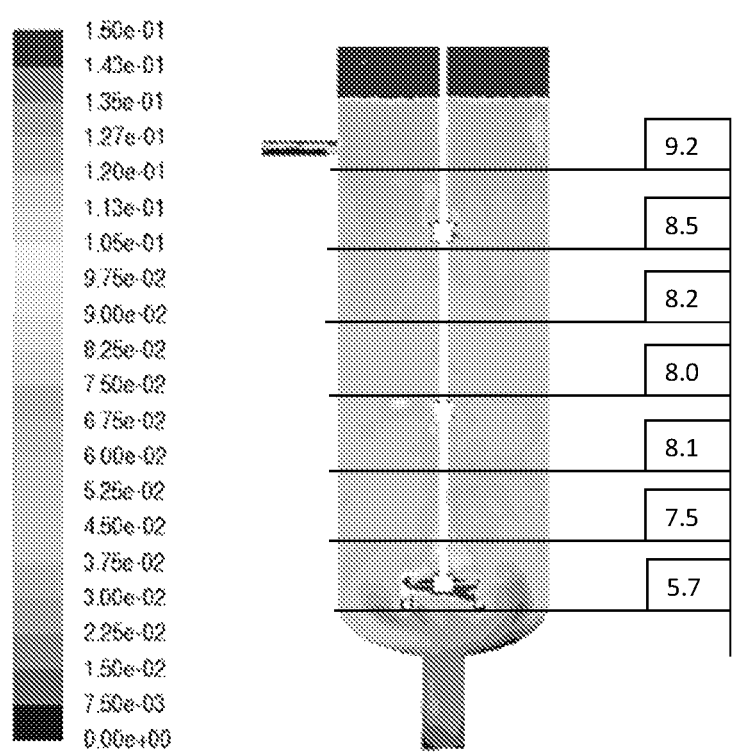
FIG. 10 shows the gas fraction distributions based on the CFD modelling for Example 4.

Another modeling experiment was performed exactly as above Example 2 except the inlet jets are oriented as a symmetrical and balanced pair of returns with dual nozzles with $\alpha=30°$ and $\beta1=\beta2=45°$. The jets were produced using simple "V" shaped plates ($\beta1=\beta2=$) 45° rotated 30° downward from the vertical)($c=30°$). In Example 4, the agitator was not operating, and two recirculation pumps are in operation (recirculation flow 1.73×). The results are shown in FIG. 10 and Table 2. There was virtually no entrainment into the recirculation loop such that the syngas "hot spot" in the bottom is reduced which leads to a very uniform gas distribution. A remarkably uniform, well mixed gas/liquid reaction fluid is observed despite the lack of an operating conventional agitator in the reactor.

TABLE 2

| | Bubble size (mm) | No. of Pumps (Relative flow rate)* | Agitator On/Off | Diverter design | Over all calc. average gas fraction | Overall average gas fraction slices | St. Dev. of slices | Impeller Power (kW) | Power due to recirculation line (kW) | % Mixing Energy from Recirculation line. | Velocity at end of return line (m/sec) | Total power per volume (kW/m³) |
|---|---|---|---|---|---|---|---|---|---|---|---|---|
| Comparative Example A (open pipe return) | 4.33 | 1 (1.0×) | On | None | 5.3 | 4.6 | 2.8 | 42.7 | 5.1 | 11 | 2.2 | 0.95 |
| Example 1 (diverter plates in pipe returns) | 1.55 | 1 (1.0×) | On | α = 90° β = 45° | 8.3 | 6.4 | 2.0 | 38.4 | 10.5 | 21 | 6.6 | 0.99 |
| Example 2 (diverter plates in pipe returns with additional pump) | 1.4 | 2 (1.73×) | On | α = 90° β = 45° | 8.0 | 6.0 | 1.3 | 44.8 | 39.3 | 47 | 10 | 1.7 |
| Example 3 (same as Example 2 but agitator not running) | 1.4 | 2 (1.73×) | Off | α = 90° β = 45°. | 7.8 | 6.5 | 1.1 | 0 | 37.0 | 100 | 9.6 | 0.75 |
| Example 4 (directed jets, agitator not running) | 1.3 | 2 (1.73×) | Off | α = 30° β = 45°. | 8.2 | 7.9 | 1.1 | 0 | 58.5 | 100 | 15.8 | 1.18 |
| Comparative Example B (Plant test similar to Example but with agitator off) | NA | 1 (1.0×) | Off | α = 90° β = 45° | NA | NA | NA | 0 | ~11 | 100 | ~7 | 0.21 |

*1.0× corresponds to 0.32 m³/s recirculation flow rate.

The above modeling results were validated in an existing facility (Comparative Example B). The facility was operated as described in Example 1 (1×) but without the agitator running. This arrangement exhibited unstable reactor operation (poor gas/liquid mixing in the reactor, poor reactor temperature/partial pressure control). When the recirculation flow rate was increased as described in Examples 2 and 3 to 1.73×, very stable reactor operation (good gas/liquid mixing in the reactor, good reactor temperature/partial pressure control) was observed even without the agitator in operation (Example 3). This established that the minimum power/volume needs to be above 10.5 kW/50 m$^3$=0.21 kW/m$^3$. A minimum power/volume should be 0.5 kW/m$^3$, above 0.7 kW/m$^3$ for some embodiments, and above 0.8 kW/m$^3$ for some embodiments.

These results demonstrate that a properly designed reaction fluid return system using a modification of a conventional recirculation loop can result in a well-mixed reaction fluid such that an agitator is not needed and can be idled or removed. This is particularly important in situations where the agitator must be shut down due to mechanical issues while the plant continues to operate. In the latter case, additional mixing energy can be supplied by increasing the flow through flow diverters by employing a spare pump, for example.

Example 5

To assess the impact of bubble size and recycle flow rate, a series of modeling experiments were performed with two recirculation flow rates (1×=0.32 m$^3$/s (single pump) and 1.73×=0.49 m$^3$/s (two pumps), respectively), a series of fixed bubble sizes, and no agitator. As with any case, the recycle flowrate and the number and size of the recirculation return nozzle(s) will determine the nozzle velocity. The results are shown in Table 3. In this case with the equipment described in Table 1, a flow rate 0.32 m$^3$/s and a 1 mm bubble size result is roughly equivalent to Example 3 above which replicated the good plant experience thus validating the CFD modelling results.

TABLE 3

|        | 0.32 m$^3$/s Flow Bubble Size | | | 0.49 m$^3$/s Flow Bubble Size | | |
|--------|------|--------|-------|------|--------|-------|
| Height | 1 mm | 4.4 mm | 10 mm | 1 mm | 4.4 mm | 10 mm |
| 0 | 3.28 | 1.25 | 0.90 | 7.36 | 2.42 | 1.67 |
| 1 | 8.69 | 1.89 | 1.08 | 9.54 | 2.97 | 1.89 |
| 2 | 9.76 | 2.69 | 1.70 | 10.20 | 3.85 | 2.36 |
| 3 | 9.86 | 3.23 | 1.90 | 10.25 | 3.75 | 2.15 |
| 4 | 9.68 | 3.54 | 2.19 | 10.17 | 3.77 | 2.39 |
| 5 | 9.69 | 3.69 | 2.34 | 10.38 | 4.05 | 2.38 |
| 6 | 9.57 | 3.86 | 2.46 | 10.40 | 4.37 | 2.45 |

Example 5 demonstrates the gas fraction and uniformity of the resulting gas/liquid mixture can be increased by decreasing the gas bubble size or increasing the flow rate in the recirculation loop.

That which is claimed:

1. A hydroformylation reaction process comprising:
   contacting an olefin, hydrogen, and carbon monoxide in the presence of a homogeneous catalyst in a vertically-oriented cylindrical reactor to provide a reaction fluid, wherein the cylindrical reactor has a fixed height, and wherein a total mixing energy of at least 0.5 kW/m$^3$ is delivered to the fluid in the cylindrical reactor;
   removing a portion of the reaction fluid from the cylindrical reactor; and
   returning at least a portion of the removed reaction fluid to the cylindrical reactor, wherein the returning reaction fluid is introduced in at least two return locations positioned at a height that is less than 80% of the fixed height, wherein the at least two return locations are positioned above a location in the reactor where hydrogen and carbon monoxide are introduced to the reactor, and wherein at least 15% of the mixing energy is provided by the returning reaction fluid.

2. The process of claim 1, wherein at least two return locations comprise one or more nozzles that protrude into the cylindrical reactor a distance of not less than 10% and not greater than 50% of the radius of the cylindrical reactor to direct the flow of the returning reaction fluid.

3. The process of claim 1, wherein the flow of the returning reaction fluid is directed by a flow diverter positioned at each return location.

4. The process of claim 3, wherein at least one flow diverter directs the flow of the returning reaction fluid horizontally.

5. The process of claim 3, wherein at least one flow diverter directs the flow of the returning reaction fluid vertically.

6. The process of claim 2, wherein the flow of the returning reaction fluid is directed by the flow diverter to prevent inducing rotational flow of the fluid around the center vertical axis of the cylindrical reactor.

7. The process of claim 2, wherein the flow of the returning reaction fluid is divided and directed in a plurality of directions that are not toward a center vertical axis of the cylindrical reactor and not perpendicular to the center vertical axis.

8. The process of claim 1, wherein the combination of the flow area of the flow diverter and the flow rate of the returning reaction fluid results in the formation of a jet of fluid inside the cylindrical reactor which imparts momentum and induces mixing in the bulk fluid in the cylindrical reactor and wherein the returning reaction fluid is divided and directed in a plurality of directions.

9. The process of claim 1, wherein hydrogen and carbon monoxide are introduced in the cylindrical reactor at a height that is less than 20% of the fixed height of the reactor, and wherein the return locations are positioned at a height that is less than 80% of the fixed height.

10. The process of claim 1, wherein hydrogen and carbon monoxide are provided as syngas, and wherein the syngas is introduced in such a manner to form discrete bubbles in the size range of less than 15 mm in diameter in the cylindrical reactor.

11. The process of claim 1, wherein a plurality of baffles are positioned inside the cylindrical reactor.

12. The process of claim 1, further comprising an agitator positioned in the cylindrical reactor.

13. The process of claim 12, wherein the agitator and the returning reaction fluid provide the mixing energy in the cylindrical reactor.

14. The process of claim 12, wherein the agitator is not operating and only the returning reaction fluid provides the mixing energy in the cylindrical reactor.

15. The process of claim 1, wherein the cylindrical reactor is a continuous stirred tank reactor (CSTR).

* * * * *